US012599484B1

(12) United States Patent
Rossi, Jr.

(10) Patent No.: US 12,599,484 B1
(45) Date of Patent: Apr. 14, 2026

(54) POLISHING DEVICE FOR ORTHOPEDIC DEVICES

(71) Applicant: Spartan Felt Company, Inc., Roebuck, SC (US)

(72) Inventor: Robert John Rossi, Jr., Spartanburg, SC (US)

(73) Assignee: Spartan Felt Company, Inc., Roebuck, SC (US)

( * ) Notice: Subject to any disclaimer, the term of this patent is extended or adjusted under 35 U.S.C. 154(b) by 558 days.

(21) Appl. No.: 17/371,396

(22) Filed: Jul. 9, 2021

Related U.S. Application Data

(60) Provisional application No. 63/049,899, filed on Jul. 9, 2020.

(51) Int. Cl.
*B24B 29/02* (2006.01)
*A61F 2/30* (2006.01)
*A61F 2/34* (2006.01)

(52) U.S. Cl.
CPC .............. *A61F 2/3094* (2013.01); *A61F 2/34* (2013.01); *B24B 29/02* (2013.01); *A61F 2310/00023* (2013.01); *A61F 2310/00239* (2013.01)

(58) Field of Classification Search
CPC ... A61F 2/3094; B24D 13/142; B24D 13/147; B24B 15/08; B24B 29/02; B24B 29/04; B24B 11/00; A47L 13/10; A47L 13/16; A47L 13/28; A47L 25/00; A61B 90/70
USPC ............................................. 451/28, 61, 532
See application file for complete search history.

(56) References Cited

U.S. PATENT DOCUMENTS

| | | | | |
|---|---|---|---|---|
| 5,369,916 A | * | 12/1994 | Jefferies | A61C 15/041 |
| | | | | 451/526 |
| 5,482,751 A | | 1/1996 | Rossi | |
| 5,525,387 A | * | 6/1996 | Rossi | B29C 70/30 |
| | | | | 428/36.1 |
| 5,885,020 A | | 3/1999 | Rossi | |
| 6,117,260 A | | 9/2000 | Rossi | |
| 7,469,474 B2 | * | 12/2008 | Farrar | A61F 2/30767 |
| | | | | 83/13 |
| 2003/0181154 A1 | * | 9/2003 | Fischer | A61C 3/06 |
| | | | | 451/532 |
| 2010/0248601 A1 | * | 9/2010 | McGrogan | A61F 2/30767 |
| | | | | 451/526 |
| 2011/0277261 A1 | * | 11/2011 | Hasket | D04H 1/413 |
| | | | | 51/298 |
| 2013/0012112 A1 | * | 1/2013 | Hsu | D04H 1/60 |
| | | | | 451/532 |
| 2014/0065935 A1 | * | 3/2014 | Ramal, Jr. | B24D 13/12 |
| | | | | 451/532 |
| 2014/0099871 A1 | * | 4/2014 | Moren | B24D 3/28 |
| | | | | 451/532 |

* cited by examiner

*Primary Examiner* — Brian D Keller
*Assistant Examiner* — Alberto Saenz
(74) *Attorney, Agent, or Firm* — Dority & Manning, P.A.

(57) ABSTRACT

Polishing devices are disclosed that are particularly well suited for polishing orthopedic implants, such as acetabular cups. The polishing device includes a polishing head having a compressible shape. The polishing head, for instance, can have a rounded surface for polishing concave surfaces. The polishing head can be made from a selection of fibers. The fibers are used to form an impregnated felt material.

8 Claims, 6 Drawing Sheets

POLISHING DEVICE FOR ORTHOPEDIC DEVICES

RELATED APPLICATIONS

The present application is based upon and claims priority to U.S. Provisional Patent Application Ser. No. 63/049,899, having a filing date of Jul. 9, 2020, which is incorporated herein by reference in its entirety.

BACKGROUND

Prosthetic devices are artificial devices used to replace or strengthen a particular part of the body. Such devices can be used in humans or animals to repair or replace diseased or damaged bone, allied tissue associated with the bone, and/or joints associated with the bone. Primarily, prosthetic devices are used to correct or prevent skeletal deformities or injuries and to alleviate the pain and discomfort associated with the deformities or injuries.

When implanting a prosthesis, typically a receiving site or cavity is first prepared in an adjoining bone. In particular, the bone can be cut and reamed out in order to accommodate the prosthesis. A bone cement is then mixed and placed in the receiving site or cavity. A prosthesis is positioned in the bone cement, and the bone cement is subsequently cured and hardened affixing the prosthesis to the bone.

Most orthopedic implants, especially joint replacements, include two cooperating parts. For example, a hip replacement typically includes a hip prosthesis that defines a head which is received within an acetabular cup. Once implanted in the body, the head of the hip prosthesis can move and rotate within the acetabular cup. Similarly, a knee replacement typically includes a tibia plateau that moves on top of a condylar implant.

In order to provide the most optimum result and comfort to the patient, the amount of friction that develops between the two adjoining parts should be as low as possible. Thus, various surfaces on orthopedic implants are polished to a high degree. For instance, in the past, cotton buffs have been used in order to polish various surfaces on orthopedic implants. Unfortunately, however, past polishing processes have not only required significant amounts of time and labor, but have also provided non-uniform results. In view of the above, a need currently exists for an improved polishing device for orthopedic implants. A need also exists for a process for using the polishing device.

SUMMARY

In general, the present disclosure is directed to a polishing device for polishing various different hard surfaces. The polishing device, for instance, can be used to polish all different types of hard materials, such as metals, gems, crystalline materials, polymers, ceramics, and the like. The polishing device of the present disclosure is particularly well suited to polishing selected surfaces on orthopedic devices. For example, the polishing device of the present disclosure can rapidly polish the surface of an orthopedic device to extremely smooth surface characteristics. In addition, the polishing device provides uniform and consistent results when polishing multiple surfaces.

In one embodiment, for instance, the present disclosure is directed to a polishing device for orthopedic devices. The polishing device includes a polishing head defining a polishing surface. The polishing surface has a rounded shape. For example, the polishing surface can have a semi-spherical shape. The polishing head further includes a base member that expands outwardly to form the polishing surface such that the polishing surface has a circumference that is larger than a circumference of the base member. The polishing head in accordance with the present disclosure is comprised of a fiber structure impregnated with a polymer impregnant. The polymer impregnant can comprise a thermoset polymer.

For example, the fiber structure that forms the polishing head can be made from thermoplastic synthetic polymer fibers, such as polyester fibers. For example, synthetic staple fibers may be used to produce the polishing head. The staple fibers can have an average length of from about 1 inch to about 4 inches, such as from about 1.5 inches to about 2.5 inches. In one embodiment, the polishing head includes different types of fibers having different characteristics. For instance, a first fiber can have a first denier and can be combined with a second fiber having a second denier. The second denier can be larger than the first denier. In one aspect, for instance, the first denier can be from about 3 to about 12, while the second denier can be from about 10 to about 25. Both fibers can comprise polyester fibers.

The impregnant, in one aspect, can contain a urethane polymer, such as a water-based urethane polymer. In one embodiment, the polishing head is formed from initially discrete layers of the fiber substrate that are then machined to a desired shape. The fiber structure can be needled prior to being impregnated with the polymer impregnant.

As described above, the base member of the polishing head expands outwardly to form the polishing surface. For example, the base member can expand at an angle to form the polishing surface. The angle can be from about 12° to about 75°. For example, in one embodiment, the angle can be from about 38° to about 75°. In an alternative embodiment, the angle can be from about 28° to about 48°. In another aspect, the angle can be from about 12° to about 32°. The angle at which the base member expands to the polishing surface can determine and control the flexibility of the polishing surface during polishing operations. Thus, the angle can be varied and changed depending upon the particular application and the desired result.

The present disclosure is also directed to a process for polishing a surface of an orthopedic device. The process includes rotating the polishing device as described above against the surface of an orthopedic device in the presence of a dope. The surface of the orthopedic device can be polished to a desired degree. For instance, the polished surface can have a surface roughness of less than about 4 RA, such as less than about 3 RA, such as less than about 2 RA, such as even less than about 1 RA. The orthopedic device can be made from a metal, such as titanium. Alternatively, the orthopedic device can be made from a zirconium. In one embodiment, the orthopedic device is an acetabular cup for use in a hip implant.

Other features and aspects of the present disclosure are discussed in greater detail below.

BRIEF DESCRIPTION OF THE DRAWINGS

A full and enabling disclosure of the present disclosure is set forth more particularly in the remainder of the specification, including reference to the accompanying figures, in which.

Figure 1:
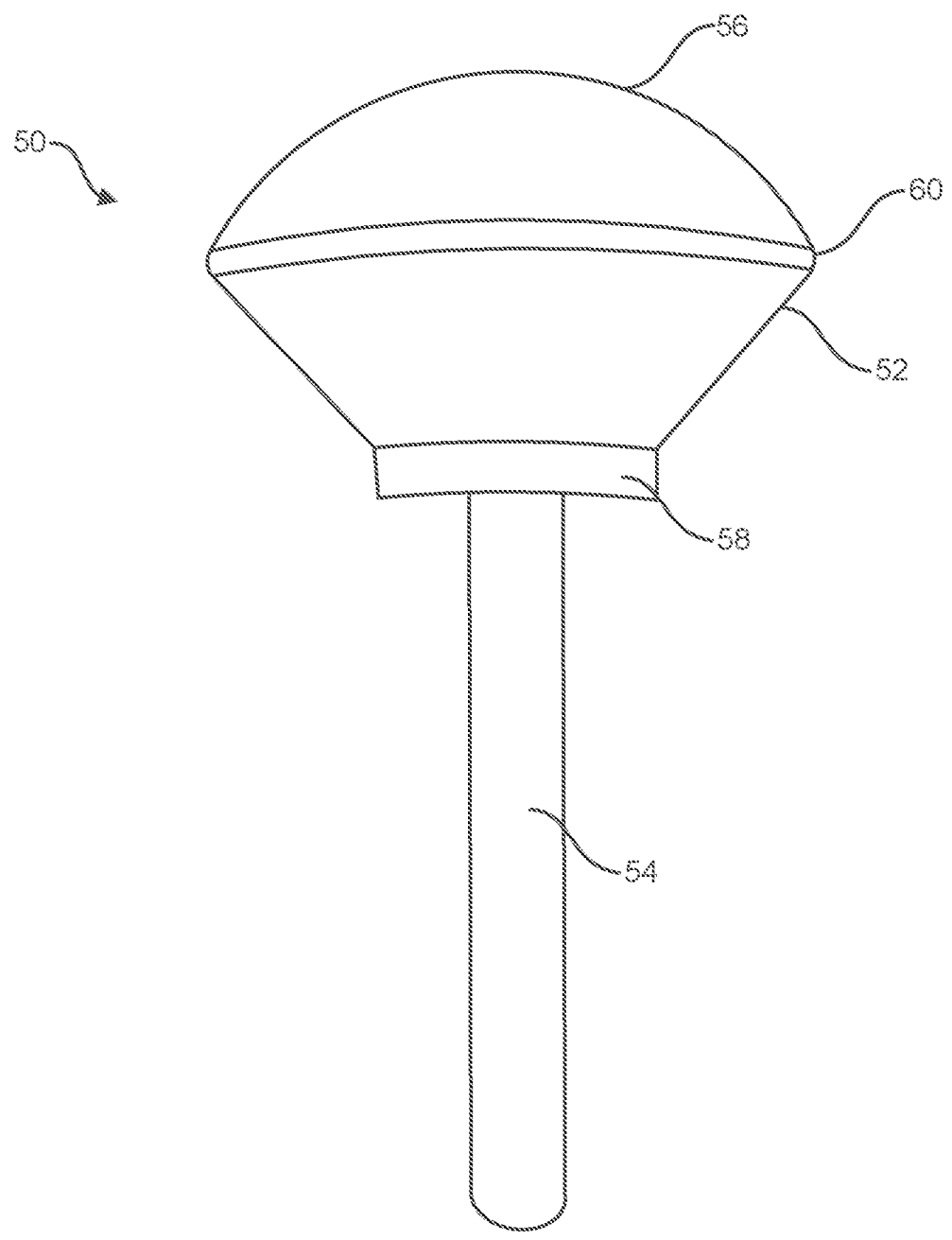
FIG. 1 is a perspective view of one embodiment of a polishing device made in accordance with the present disclosure.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present disclosure.

In general, the present disclosure is directed to a polishing device having a unique shape that makes the device well suited to polishing various different surfaces, including concave surfaces. The polishing device can be used to polish diverse and numerous different materials. For example, the polishing device can be used to polish metals, gems, polymers such as crystalline polymers, ceramics, and the like. The polishing device is particularly well suited to polishing transition metals, such as titanium and zirconium.

In one aspect, the polishing device of the present disclosure can be formed from a fiber structure. The fiber structure, for instance, can comprise a nonwoven, felt material containing synthetic polymer fibers. The fiber structure can be impregnated with an impregnant comprising a thermoset polymer. The fiber structure can be formed, impregnated, and then machined into a shape that facilitates polishing various materials, especially in the presence of a dope.

Alternatively, the polishing device can be a cast product that optionally contains fibers and primarily comprises the polymer impregnant.

The polishing device of the present disclosure can provide various advantages and benefits in relation to conventional polishing materials. For instance, it was discovered that the polishing device of the present disclosure can polish hard surfaces, such as metal surfaces, very rapidly. Of particular advantage, the polishing device is capable of being reused and polishing multiple surfaces, wherein the polished surfaces having uniform characteristics.

In one aspect, the polishing device of the present disclosure can be used to polish orthopedic or prosthetic devices. For example, referring to FIGS. 5 and 6, a total hip implant is illustrated. The hip implant includes a hip prosthesis 10 having a stem 12 and a head 14. Hip prosthesis 10 can be made from any suitable material, such as a metal. For example, the hip prosthesis 10 can be made from titanium. As shown, hip prosthesis 10 has been inserted into a cavity defined by a bone 16, such as a femur.

Especially when constructed from a metal, the hip prosthesis 10 can include a precoat layer 18 that bonds with a bone cement 20. The bone cement 20 attaches the hip prosthesis 10 to the bone 16.

Figure 5:
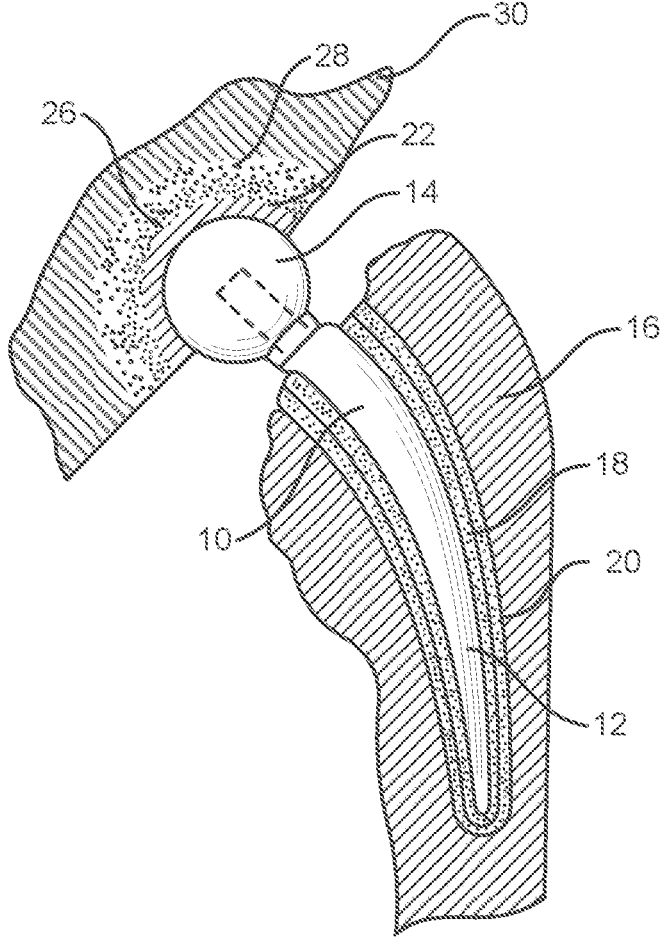
FIG. 5 is a cross-sectional view of one embodiment of a hip implant.

The hip implant illustrated in FIG. 5 further includes an acetabular cup 22. The acetabular cup 22 can be made from the same material as the hip prosthesis 10 or from a different material. The acetabular cup 22 can also include a precoat material 26 that forms a tie layer between the acetabular cup 22 and a bone cement 28. The bone cement 28 is for attaching the acetabular cup 22 to a hip bone 30.

Figure 6:
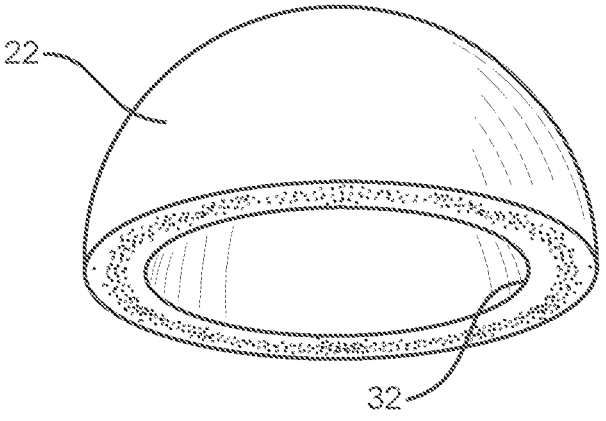
FIG. 6 is a perspective view of an acetabular cup that is incorporated into the hip implant illustrated in FIG. 5.

Referring to FIG. 6, acetabular cup 22 is shown in greater detail. Acetabular cup 22 includes an inner surface 32 that is designed to engage with the head 14 of the hip prosthesis 10. The head 14 and the interior surface 32 of the acetabular cup 22 form a cooperating relationship when implanted into a body. The implant is designed such that the head 14 can freely rotate within the acetabular cup 22. As shown, the inner surface 32 of the acetabular cup 22 has a concave shape that is particularly well suited to surrounding a portion of the head 14 of the hip prosthesis 10. When engaged together and moving relative to each other, the surface of the head 14 and the interior surface 32 of the acetabular cup 22 preferably create a low friction engagement. Consequently, the surface of the head 14 and particularly the interior surface 32 of the acetabular cup 22 are polished to a very high degree in order to minimize surface roughness. The polishing device of the present disclosure is particularly well suited to polishing the interior surface 32 of the acetabular cup 22. The polishing device of the present disclosure, however, can also be used to polish any portion of the hip prosthesis 10.

For example, referring to FIG. 1, one embodiment of a polishing device 50 made in accordance with the present disclosure is shown. The polishing device 50 includes a polishing head 52 attached to a stem 54. The stem 54 can be integral with the polishing head 52 or can be otherwise attached to the polishing head 52. For example, in one embodiment, the stem 54 can be made from a metal, such as stainless steel. The stem 54 is for engaging with a polishing machine for rotating the polishing head 52.

As shown in FIG. 1, the polishing head 52 includes a polishing surface 56. The polishing surface 56 has a three-dimensional, rounded shape. For instance, in one embodiment, the polishing surface 56 can have a semi-spherical shape. The polishing surface 56, for instance, can have a shape that is well suited for polishing an adjacent surface. For example, as shown in FIG. 6, the polishing surface 56 of the polishing device 50 can have a shape that is well suited for being inserted into the concave surface 32 defined by the acetabular cup 22.

In one aspect, the base member 58 of the polishing device 50 can expand outwardly to form the polishing head 52 and the polishing surface 56. In this manner, the circumference of the base member 58 is smaller than a circumference 60 of the polishing surface 56. For example, the circumference 60 of the polishing surface 56 can be at least 30% greater, such as at least 50% greater, such as at least 70% greater, such as at least 90% greater, such as at least 110% greater, such as at least 130% greater, such as at least 150% greater, such as at least 170% greater, such as at least 190% greater, such as at least 210% greater, such as at least 250% greater than the circumference of the base member 58. The circumference 60 of the polishing head 56 is generally less than about 600%, such as less than about 400% of the circumference of the base member 58. Designing the base member 58 to have a smaller circumference than the polishing surface 56 can provide various advantages when the polishing device is placed in service. For example, by having the base member 58 smaller than the circumference 60 of the polishing surface 56, the polishing surface 56 can better flex and conform to the surface being polished. The shape of the polishing head 52, for instance, allows the polishing surface to be compressible which has been found to greatly enhance the polishing process.

In the embodiment illustrated in FIG. 1, the base member 58 expands outwardly at an angle to form the polishing surface 56. This angle and the shape of the polishing surface 56 can be altered and varied depending upon the particular application. As an example, there are over 16 different sizes of acetabular cups that are sold and produced by one orthopedic device maker. Consequently, the polishing head 52 can be altered and varied depending upon the objects to be polished.

Figure 2:
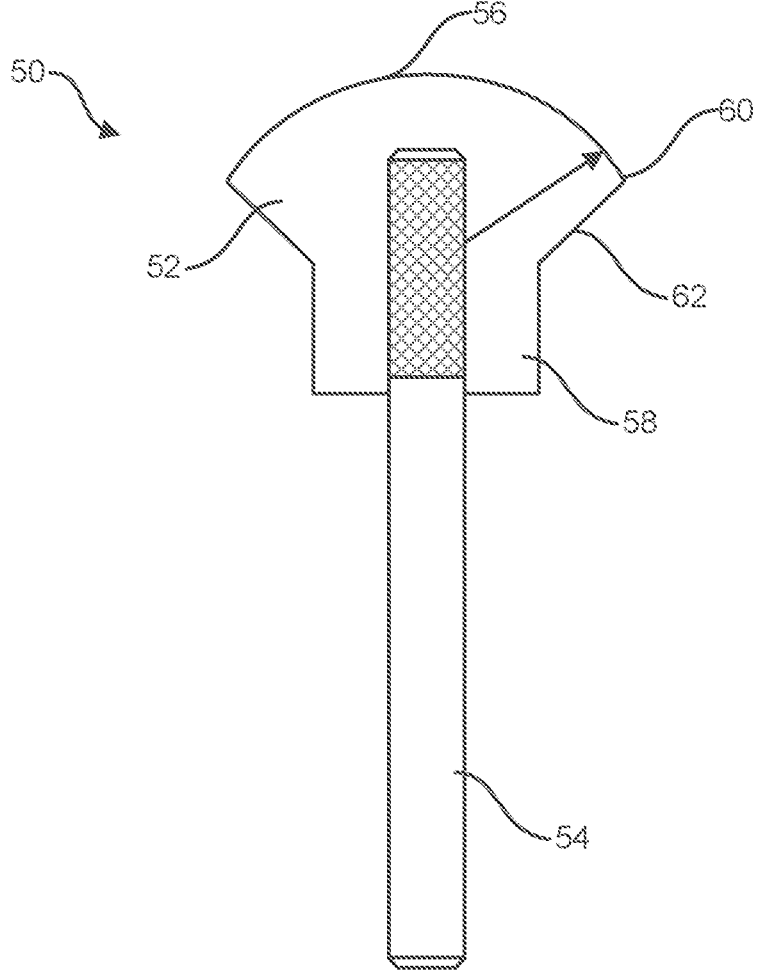
FIG. 2 is a cross-sectional view of the polishing device illustrated in FIG. 1.
Figure 3:
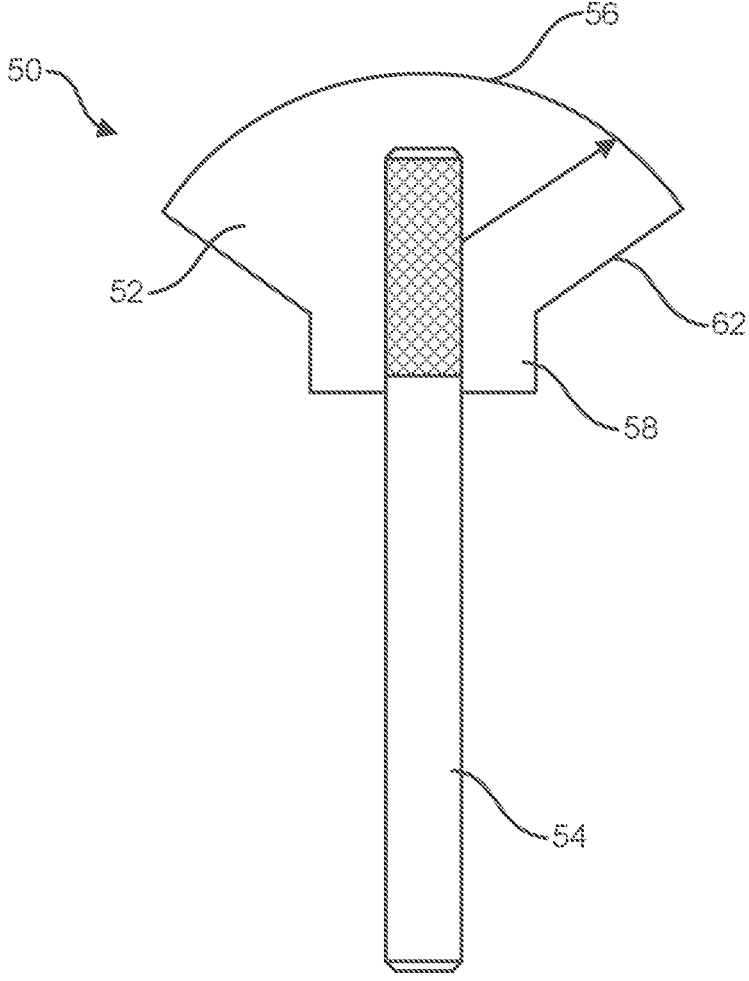
FIG. 3 is a cross-sectional view of another embodiment of a polishing device made in accordance with the present disclosure.
Figure 4:
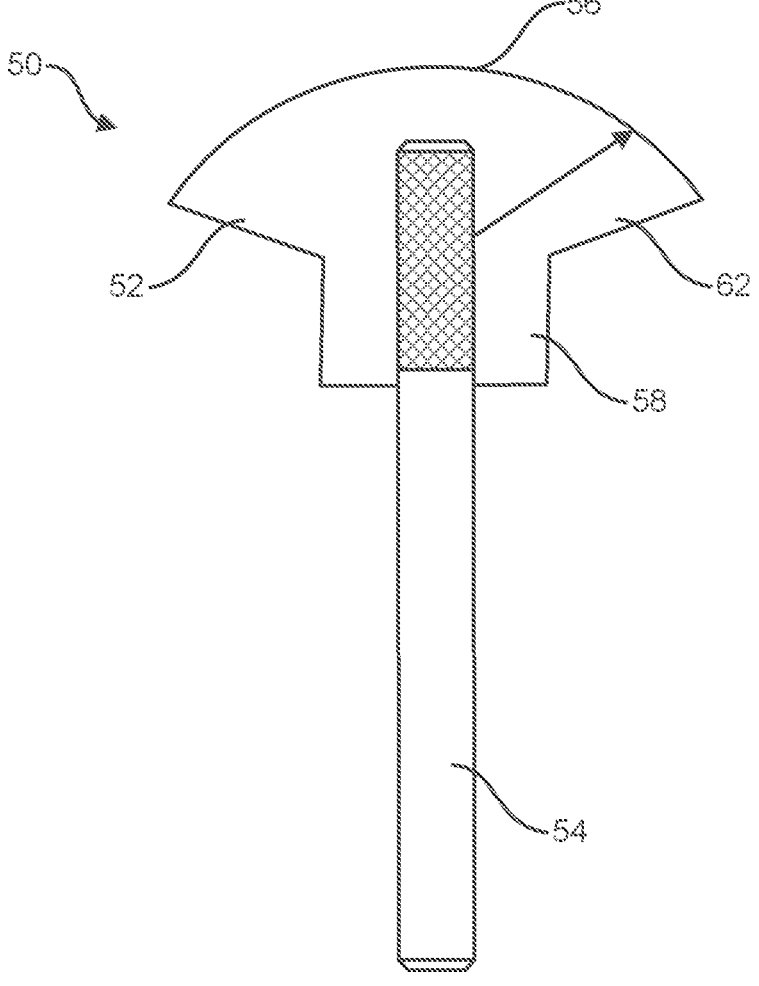
FIG. 4 is a cross-sectional view of another embodiment of a polishing device made in accordance with the present disclosure.

Referring to FIGS. 2-4, for instance, different exemplary embodiments of polishing devices made in accordance with the present disclosure are shown. Like reference numerals have been used to indicate similar elements. In FIGS. 2-4, the shape of the polishing head 52 is varied primarily by varying the angle between the base member 58 and the polishing surface 56.

Referring to FIG. 2, for instance, polishing device 50 includes a polishing head 52 mounted on a stem 54. The polishing head 52 includes a base member 58 that expands along an angular surface 62 to form a polishing surface 56 having a circumference 60. The angular surface 62 can extend from the base member 58 generally at an angle of from about 12° to about 75°, including all increments of 1° therebetween. In the embodiment illustrated in FIG. 2, for instance, the angular surface 62 forms an angle of approximately 45° with a horizontal line perpendicular to the axis of the stem 54 that intersects the base member 58.

The angle between the base member 58 and the polishing surface 56, however, can be controlled and manipulated depending upon the particular application. For instance, the angle can be greater than about 12°, such as greater than about 15°, such as greater than about 18°, such as greater than about 20°, such as greater than about 23°, such as greater than about 25°, such as greater than about 28°, such as greater than about 30°, such as greater than about 33°, such as greater than about 35°, such as greater than about 38°, such as greater than about 40°, such as greater than about 43°, such as greater than about 45°, such as greater than about 48°, such as greater than about 50°, such as greater than about 53°, such as greater than about 55°, such as greater than about 58°, such as greater than about 60°, and generally less than about 75°, such as less than about 70°. In one aspect, the angle can be from about 38° to about 75°. In another aspect, the angle can be from about 28° to about 48°. In still another aspect, the angle can be from about 12° to about 32°.

As indicated above, the angle in FIG. 2 is approximately 45°. Referring to FIG. 3, a similar polishing device 50 is illustrated in which the angular surface 62 extends at an angle of approximately 35° from the base member 58 to the polishing surface 56. In FIG. 4, on the other hand, the angular surface 62 is at an angle of about 20° from the base member 58 to the polishing surface 56. As shown in FIGS. 2-4, reducing the angle of the angular surface 62 causes the polishing surface 56 to fan out to a greater degree. Thus, decreasing the angle between the base member 58 and the polishing surface 56 can increase the surface area of the polishing surface 56. Reducing the angle can also increase the flexibility and compressibility of the polishing head 52.

The polishing head 52 is formed from, in one embodiment, a fiber structure that has been impregnated with a thermoset resin. For example, the polishing head can be made from staple fibers, particularly polymeric synthetic staple fibers. The size or denier of the fibers can be selected depending upon the desired density of the final material and the coarseness of the polishing surface. In one aspect, the polishing head is formed from polyester fibers, such as mono-component polyester fibers.

The denier of the fibers used to make the polishing head can generally be greater than about 1, such as greater than about 3, such as greater than about 5, such as greater than about 7, such as greater than about 9, and generally less than about 20, such as less than about 15, such as less than about 12, such as less than about 10. The average length of the fibers can generally be greater than about 0.5 inches, such as greater than about 1 inch, such as greater than about 1.5 inches, such as greater than about 1.75 inches, and generally less than about 4 inches, such as less than about 3.5 inches, such as less than about 3 inches, such as less than about 2.5 inches, such as less than about 2 inches.

In one particular aspect, the polishing head is formed from a first fiber combined with a second fiber. The second fiber can have a denier greater than the first fiber. For instance, the denier of the first fiber can be from about 3 to about 12, such as from about 4 to about 8, while the denier of the second fiber can be from about 10 to about 25, such as from about 12 to about 18. Both fibers can comprise monocomponent polyester fibers. The first and second fibers can be present in the polishing head at a weight ratio of from about 30:70 to about 70:30, such as from about 40:60 to about 60:40.

Forming the polishing head from first fibers and second fibers with different deniers can provide various advantages and benefits. For example, the different size fibers can produce an optimum pore structure which captures debris during the polishing process.

In order to produce the polishing head, the fibers are first formed into a nonwoven, felt substrate. For instance, the fibers can be carded so as to align the fibers in substantially one direction. After a carded web is formed, the carded web can be cross-lapped in order to increase the thickness and create a material having a desired weight per unit area. The cross-lapped structure can have from about 2 to about 20 layers of material.

The carded and cross-lapped nonwoven is then passed through a needle loom. The needle loom can include a plurality of fine needles mounted on one or more needle boards. The needle boards can reciprocate causing the needles to penetrate the nonwoven and entangle the fibers for forming a consolidated substrate with felt properties. The types of needles used during the needling process and the needle density can vary depending upon the desired density of the final material. One embodiment of a needling process is described in U.S. Pat. No. 6,117,260, which is incorporated herein by reference.

After needling, a stiffened felt-like substrate material is produced. The felt-like substrate can be in the form of sheets. In order to produce the polishing head of the present disclosure, the felt-like material is impregnated with a resin solution, such as a thermoset resin solution. In one aspect, for instance, the felt-like material can be submerged in a bath containing the impregnant.

The impregnant may comprise any suitable polymer material, such as a thermoset polymer material. The thermoset polymer material can be a urea-formaldehyde melamine, an epoxy or the like. In one aspect, the bath contains water in conjunction with the impregnant. For instance, the bath can contain a water-based melamine solution or a water-based urethane solution. In one aspect, the bath contains a water-based urethane or water-based melamine in combination with a polycarbonate. Water can be contained in the bath in an amount from about 30% to about 70% by weight, such as in an amount from about 40% to about 60% by weight. In addition to water-based baths, the impregnant may also be contained in a solvent.

After the felt-like material is impregnated, the material can be passed through a rotary press to remove excess solution. In general, any suitable press can be used. The wet weight of the material after being pressed is generally less than twice the dry weight of the material.

After being pressed, the impregnated material is placed in an oven in order to cure the impregnant. The temperature and time at which the material stays in the oven is dependent upon the particular impregnant used. In one aspect, for instance, the material can be placed in an oven at a temperature of from about 120° F. to about 300° F. for a time of from about 30 minutes to about 4 hours.

After curing, the felt-like sheet resembles a consolidated material, even if multiple layers have been used to produce the material. After being impregnated and cured, for instance, the different layers become indistinguishable. If desired, the impregnated material can be optionally pressed to a desired thickness. For instance, the material can be pressed at a pressure of from about 800 psi to about 1500 psi in order to change the properties of the material if desired.

After curing, the impregnant generally comprises from about 10% to about 90% of the weight of the resulting material. For instance, the impregnant can be greater than about 20%, such as greater than about 30%, such as greater than about 40%, and generally less than about 80%, such as less than about 70%, such as less than about 60% of the weight of the final material.

After the felt-like material is impregnated and cured, the resulting material can then be formed into the desired shape in order to create the polishing head of the present disclosure. For example, in one aspect, the material can be sliced into rectangular blocks that then can be machined to the desired shape. For example, the material can be subjected to a grinding process in order to produce the polishing surface having the rounded shape. In one embodiment, the material can be fed into different grinding processes for producing the overall shape as shown in the figures. In one embodiment, a plunge grinder can be used that contains a grinding wheel shaped to produce the polishing head. Each of the grinding processes can be done according to a dry process or according to a wet grinding technique.

Alternatively, the fibrous material can be molded into a particular shape and then impregnated. In this embodiment, the product can be cast into the desired shape and may optionally contain fibers.

Polishing devices made in accordance with the present disclosure have been found to provide numerous advantages and benefits. As described above, the polishing devices are particularly well suited to polishing orthopedic implants. The polishing device of the present disclosure has been found to be well suited to polishing a metal surface to a surface roughness of less than about 4 RA, such as less than about 3 RA, such as less than about 2 RA, such as even less than about 1 RA. The resulting metal surface, for instance, can be greater than 10% reflective, such as greater than about 20% reflective, such as even greater than about 30% reflective.

The polishing device of the present disclosure is also extremely efficient. For instance, metal surfaces can be polished using a dope in less than about 5 minutes, such as less than about 3 minutes, such as even less than about 1 minute. As a comparison, past conventional polishing materials typically took greater than 6 minutes in order to polish the surfaces. The polishing device of the present disclosure not only works much faster but also produces more uniform results.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A method for polishing orthopedic devices comprising: rotating a polishing device against a surface of an orthopedic device in the presence of a dope, the orthopedic device comprising an acetabular cup of a hip implant, the surface comprising a concave surface of the acetabular cup, the concave surface comprising titanium or zirconium, the polishing device having a three-dimensional, rounded shape that is inserted into the concave surface of the acetabular cup, the polishing device including a polishing head defining a polishing surface, the polishing head including a base member that expands outwardly to form the polishing surface such that the polishing surface has a circumference that is larger than a circumference of the base member, the polishing head comprising a fiber structure impregnated with a polymer impregnant, the fiber structure comprising a felt substrate, the polymer impregnant comprising a thermoset polymer, wherein the polymer impregnant is present in the polishing head in an amount greater than 20% by weight of the polishing head, wherein the fiber structure includes a first fiber and a second fiber, the first fiber having a first denier and the second fiber having a second denier, the second denier being greater than the first denier, and wherein the polishing head is rotated against the surface of the acetabular cup until the surface displays a surface roughness of 2 RA or less.

2. The method as defined in claim 1, wherein the orthopedic device is polished in 5 minutes or less.

3. The method as defined in claim 1, wherein the orthopedic device is polished in 3 minutes or less.

4. The method as defined in claim 1, wherein the polishing head is only made from polymer synthetic staple fibers and the impregnant.

5. The method as defined in claim 1, wherein the surface of the orthopedic device is polished to a roughness of 1 RA or less.

6. The method as defined in claim 1, wherein the base member expands at an angle to form the polishing surface, the angle being from 38° to 75°.

7. The method as defined in claim 1, wherein the first fiber comprises polyester fibers and the second fiber comprises polyester fibers.

8. The method as defined in claim 1, wherein the denier of the first fiber is from 3 to 12 and the denier of the second fiber is from 10 to 25.

* * * * *